United States Patent
Saydoff

(10) Patent No.: US 6,407,204 B1
(45) Date of Patent: Jun. 18, 2002

(54) USE OF CONANTOKINS FOR PRODUCING ANALGESIA OR FOR NEUOPROTECTION

(75) Inventor: Joel Saydoff, Barrington, RI (US)

(73) Assignee: CytoTherapeutics, Inc., Lincoln, RI (US)

( * ) Notice: Subject to any disclaimer, the term of this patent is extended or adjusted under 35 U.S.C. 154(b) by 0 days.

(21) Appl. No.: 09/120,759

(22) Filed: Jul. 22, 1998

Related U.S. Application Data

(62) Division of application No. 08/847,848, filed on Apr. 28, 1997, now Pat. No. 5,844,077.

(51) Int. Cl.$^7$ .............................................. A61K 38/10
(52) U.S. Cl. .................... 530/326; 604/891.1; 424/422; 514/12; 514/13; 514/14; 435/70.1; 530/324; 530/325
(58) Field of Search ................................ 530/326, 325, 530/324; 514/12–14

(56) References Cited

U.S. PATENT DOCUMENTS

| | | | |
|---|---|---|---|
| 5,364,842 A | 11/1994 | Justice | 514/12 |
| 5,432,155 A | 7/1995 | Olivera | 514/12 |
| 5,523,323 A | 6/1996 | Maccecchini | 514/531 |
| 5,587,454 A | 12/1996 | Justice | 530/324 |
| 5,854,217 A | * 12/1998 | MacCeccmini | |

FOREIGN PATENT DOCUMENTS

| | | |
|---|---|---|
| WO | WO 94/06455 | 3/1994 |
| WO | WO 94/07914 | 4/1994 |
| WO | 96/11698 | * 4/1996 |
| WO | WO 98/03189 | 1/1998 |
| WO | WO 98/03541 | 1/1998 |

OTHER PUBLICATIONS

Advokat et al., *Brain Research*, 641, 135–140 (1994).
Anson et al., *Letters to Nature*, vol. 315, 683–685 (1985).
Berge t al., *Experimental Cell Research*, 192, 32–40 (1991).
Carter et al., *The Journal of Pharmacology and Experimental Therapeutics*, vol. 253, No. 2, 275–482 (1990).
Chandler et al., *The Journal of Biological Chemistry*, vol. 268 No. 23, 17173–17178 (1993).
Coderre, *APS Journal*, vol. 3, No. 4, 232–239 (1994).
Coderre, *European Journal of Neuroscience*, vol. 5, 390–393 (1993).
Coderre, *Pain*, 59, 353–359 (1994).
Coderre, *European Journal of Neuroscience*, vol. 5, 390–393 (1993).
Dickenson et al., *Gen. Pharmac.*, vol. 28, No. 5, 633–638 (1997).
Dickson et al., *Trends in Pharmacological Sciences*, vol. III, 307–309 (1990).
Elliott et al., *Pain*, 59, 361–368 (1994).
Felby et al, *Pain*, 64, 283–291, (1995).
Feng et al., *Pain*, 66, 343–349 (1996).
Furuyama et al., *Molecular Brain Research*, 18, 141–151 (1993).
Haack et al., *Neuroscience Letters*, 163, 63–66 (1993).
Hammerland et al., *European Journal of Pharmacology–Molecular Pharm. Section*, 226, 239–244 (1992).
Hao et al., *Pain*, 66, 279–285 (1996).
Henry et al., *APS Journal*, 3 (4), 249–256 (1994).
Hoffman et al., *Neuropharmacology and Neurotoxicology*, vol. 7, No. 3, 838–840 (1996).
Hunter et al., *Neuroscience Letters*, 174, 217–221 (1994).
Malmberg et al., *Pain*, 291–300 (1993).
McIntosh et al, *The Journal of Biological Chemistry*, vol. 259, No. 23, 114343–114346 (1984).
Mena et al., *Neuroscience Letters*, 118, 241–244 (1990).
Michaelis, *Neural Notes*, vol. II, 2, 3–7 (1996).
Miltan et al., *Neuroscience Letters*, 178, 139–143 (1994).
Murray et al., *Pain*, 44, 179–185 (1991).
Nasstrom et al., *European Journal of Pharmacology*, 212, 21–29 (1992).
Nikolajsen et al., *Pain*, 67, 69–77 (1996).
Perrault, et al., *European Journal of Pharmacology*, 183, 942 (1990).
Skolnick et al., *Journal of Neurochemistry*, vol. 59, No. 4, 1516–1521 (1992).
Skolnick et al., *Conantokin–G and Its Analogs:*, Chapter 11, 155–165, CRC Press (1994).
Steinberg et al., *Journal Neurosurg.*, 84, 860–866 (1996).
Vaccarino et al., *Brain Research*, 615, 331–334 (1993).
Walls et al., *Brain Research*, 670, 342–346 (1995).
Xu et al., *Gene*, 81, 139–149 (1989).
Zhou et al, *Neurosci.*, "Synthetic Conantokins: Novel Polyamine Antagonists of the NMDA Receptor Complex", (1996).

* cited by examiner

Primary Examiner—Christopher S. F. Low
Assistant Examiner—David Lukton
(74) *Attorney, Agent, or Firm*—Ivor R. Elrifi; Michel Morency; Mintz, Levin, Cohn, Ferris Glovsky & Popeo, P.C.

(57) ABSTRACT

A method for producing analgesia or for neuroprotection in a mammal comprising administering a therapeutically effective amount of a conantokin to the mammal.

8 Claims, 7 Drawing Sheets

USE OF CONANTOKINS FOR PRODUCING ANALGESIA OR FOR NEUOPROTECTION

This application is a divisional of application Ser. No. 08/847,848, filed Apr. 28, 1997, now U.S. Pat. 5,844,077.

TECHNICAL FIELD OF THE INVENTION

This invention relates to administration of a therapeutically effective amount of one or more conantokin molecules for production of analgesia or for neuroprotection.

BACKGROUND OF THE INVENTION

Chronic or intractable pain, which may result from degenerative conditions or debilitating diseases, is currently treated with a variety of analgesic compounds, often opioid compounds such as morphine. Likewise, neuropathic pain, typically a chronic condition attributable to injury or partial transection of a peripheral nerve, is also conventionally treated with opioid compounds such as morphine.

Conventional therapies for pain produce analgesia—a loss of sensitivity to pain without the loss of consciousness. Opioid compounds have been used widely to produce analgesia, including plant-derived opioids such as morphine, and endogenous opioids such as met- and leu-enkephalins, as well as β-endorphin.

Opioid compounds, while effective in producing analgesia for many types of pain, may induce tolerance in some patients. When a patient becomes tolerant, increasing doses of the opioid are required to produce the desired analgesic effect. In addition, these compounds frequently result in a physical dependence in patients, and may have side effects at high doses.

The treatment of painful conditions with NMDA receptor antagonists acting at various sites on the NMDA receptor/channel complex has been limited due to side effects or inactivity. Reports suggest that NMDA antagonists at the channel site may be useful in preventing the development of tolerance (Marek et al. "Excitatory amino acid antagonists (kynurenic acid and MK-801) attenuate the development of morphine tolerance in the rat", *Brain Res.*, 547, pp. 77–81 (1991); Elliott et al., "Dextromethorphan attenuates and reverses analgesic tolerance to morphine", *Pain*, 59, pp. 361–368. (1994); Mao et al., "Thermal hyperalgesia in association with the development of morphine tolerance in rats: roles of excitatory amino acid receptors and protein kinase", *J.Neurosci.*, 14, pp. 2301–2312 (1994); Manning et al., "Continuous co-administration of dextromethorphan or MK-801 with morphine: attenuation of morphine dependence and naloxone-reversible attenuation of morphine tolerance", *Pain*, 67, pp. 79–88 (1996).

The analgesic effects and adverse actions of various NMDA receptor antagonists has been shown to vary depending on the site of action and potency of the drug. For example, NMDA receptor antagonists acting at the ion channel in a noncompetitive manner (e.g., MK-801 and phenylcyclidine (PCP)) or competitive inhibitors, show analgesic activity but show motor impairment at equivalent doses (Nasstrom et al., "Antinociceptive actions of different classes of excitatory amino acid receptor antagonists in mice", *Eur. J. Pharm.*, 212, pp. 21–29(1992); Coderre, "Potent analgesia induced in rats by combined action at PCP and polyamine recognition sites of the NMDA receptor complex" *Eur. J. Neurosci.* 5, pp. 390–393 (1993); Milan and Seguin, "Chemically-diverse ligands at the glycine B site coupled to N-methyl-D-aspartate (NMDA) receptors selectively block the late phase of formalin-induced pain in mice", *Neurosci. Lett.*, 178, pp. 139–143 (1994); Yamamoto and Yaksh, "Spinal pharmacology of thermal hyperesthesia induced by incomplete ligation of sciatic nerve", *Anesthesiol.*, 75, pp. 817–826 (1991); Yamamoto and Yaksh, "Comparison of the antinociceptive effects of pre- and posttreatment with intrathecal morphine and MK801, an NMDA antagonist, on the formalin test in the rat", *Anesthesiol.*, 77, pp. 757–763 (1992). Glycine B-site NMDA antagonists appear to have analgesic activity at doses that do not impair motor function (Milan and Seguin, 1994).

Importantly, polyamine site NMDA antagonists (e.g. ifenprodil) did not have an analgesic effect in the formalin test, even when administered at a high dose (Coderre, 1993, supra). This invention provides a family of polyamine-site NMDA antagonist compounds, the conantokins, that do have analgesic effects, and at doses which do not produce overt side effects.

NMDA ion channels are thought to mediate neurotoxicity in many acute and chronic neurodegenerative diseases by overexcitation and excessive calcium entry into nerve cells. Such neurodegenerative disorders include epilepsy, stroke, Parkinson's disease, Huntington's disease and Alzheimer's disease. Methods of preventing or neuroprotecting against such excitoxicity would be desireable. This invention also provides a family of polyamine-site NMDA antagonist compounds, the conantokins, that exhibit neuroprotective effects against excitotoxic damage mediated at least in part by NMDA receptors.

Conantokins are a family of peptides from the Conus snail that are 10–30 amino acids with antagonist activity at the polyamine site of the NMDA receptor. These peptides do not normally contain disulfide residues like other peptides found in Conus venom. The conantokin peptides typically contain the modified amino acid gamma-carboxyglutamate (Gla).

The methods of this invention may be useful in the treatment of pain (whether acute or chronic), including chronic pain, and neuropathic pain, without undesirable side effects. In addition, continuous administration of a conantokin combined with an opioid agonist, may be useful in preventing the development of tolerance of patients to opioid compounds.

The methods of this invention may also be useful for neuroprotection against excitotoxic damage mediated at least in part by NMDA receptors.

SUMMARY OF THE INVENTION

This invention provides novel methods and devices for treating pain by administering a conantokin molecule, preferably directly into the patient's central nervous system ("CNS"), most preferably intrathecally. If administered directly to the central nervous system, the dosage contemplated is between about 1 ng–100 mg per day, preferably between about 100 ng–10 mg per day, most preferably between 1 μg and 100 μg per day. If administered peripherally (preferably intravenously), the dosage contemplated is somewhat higher, between about 100 ng–1000 mg per day, preferably between about 10 μg–100 μg per day, most preferably between 100 μg and 10 mg per day.

This invention also provides novel methods and devices for neuroprotection against excitotoxicity mediated at least in part by NMDA receptors. We contemplate similar dosages of conantokin as outlined above for treatment of pain, if delivered directly to the central nervous sytem. Higher dosages for neuroprotection using a conantokin are contemplated for peripheral delivery, between 100 ng to 10,000 mg per day, preferably intravenously or intra-arterially.

In one embodiment, the conantokin is selected from the group consisting of con antokin-G, conantokin-T, con antokin-R, con antokin-Oc, conantokin-Si, and muteins, analogs or active fragments, of the foregoing conantokins.

DETAILED DESCRIPTION OF THE INVENTION

Figure 1:
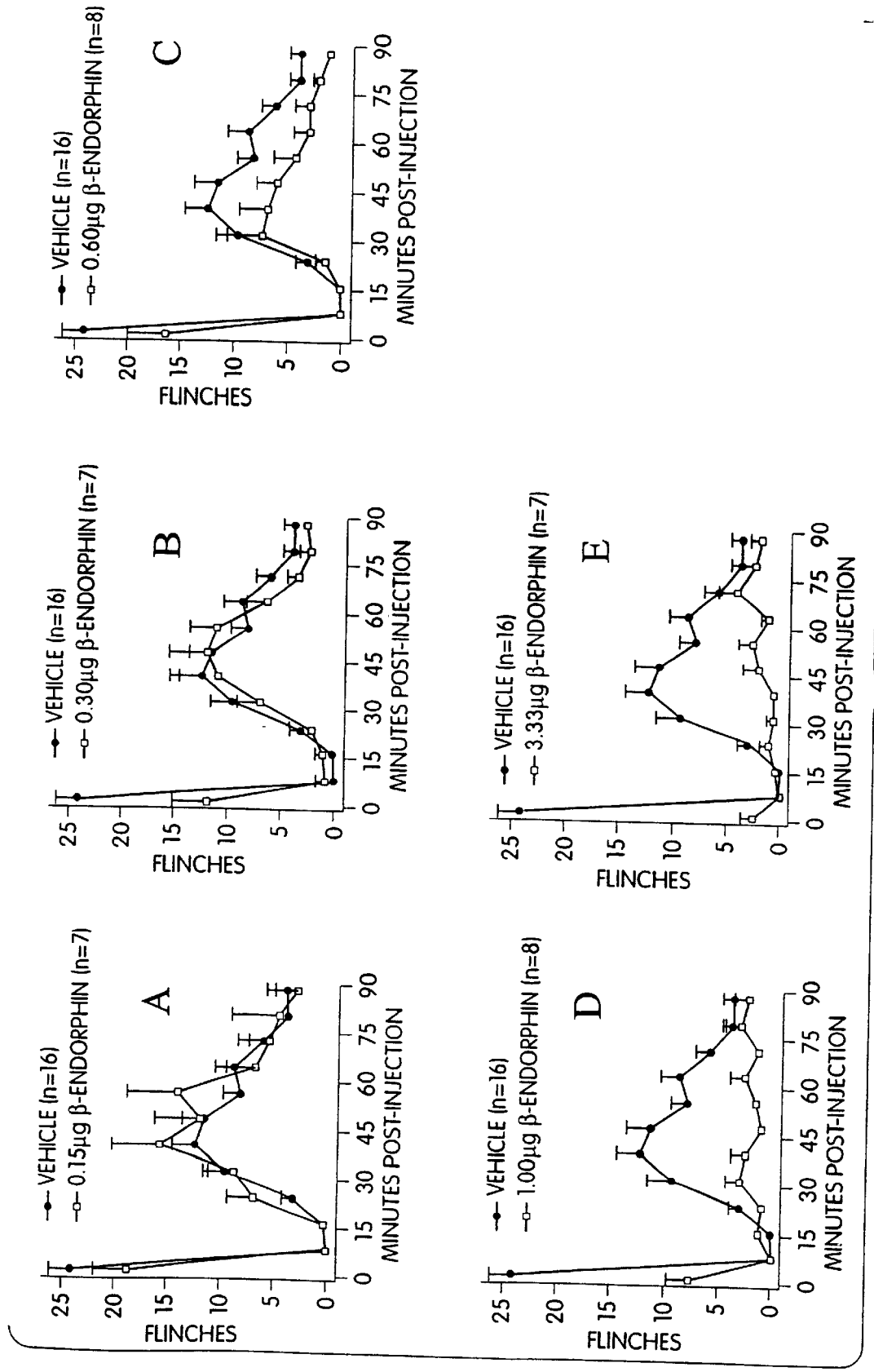
FIGS. 1A–E shows results (plotted as hindpaw flinches versus time) in the formalin test for pain comparing beta-endorphin and controls, for dosages of beta-endorphin of 0.15 μg (Panel A), 0.30 μg (Panel B), 0.60 μg (Panel C), 1.00 μg (Panel D) and 3.33 μg (Panel E).

This invention relates to administration of one or more conantokin molecules for the treatment of pain or for neuroprotection.

The conantokins useful in this invention are defined as those conanatokin peptides that act as antagonists at the polyamine site of the NMDA receptor. The conantokin fractions isolated to date include conantokin-G, conantokin-T, conantokin-R, conantokin-Oc, and conantokin-Si. Conantokins typically have 10–30 amino acids.

Muteins, analogs or active fragments, of the foregoing conantokins are also contemplated here. See, e.g., Hammerland et al, Eur. J. Pharmacol., 226, pp. 239–244 (1992).

In one preferred embodiment, conantokin-G ("con-G"), or a mutein, analog or active fragment thereof, is administered to produce analgesia or for neuroprotection. Conantokin-G has 17 amino acids and contains five negatively charged γ-carboxyglutamate residues ("Gla residues"). See, e.g., McIntosh et al., J. Biol. Chem., 259, pp. 14343–346 (1984). Some of these Gla residues appear to be substitutable with no loss of biological activity. However, gamma carboxylation of at least 2 glutamate residues (AA3 and AA4) appear to be required for biological activity (Chandler et al., "Polyamine-like actions of peptides derived from conantokin-G, an N-methyl-D-aspartate (NMDA) antagonist", J. Biol. Chem., 268, pp. 17173–17178 (1993). Conantokin-G has the following amino acid sequence:

Con-G Gly-Glu-Gla-Gla-Leu-Gln-Gla-Asn-Gln-Gla-Leu-Ile-Arg-Gla-Lys-Ser-Asn-NH$_2$ (SEQ. ID. NO. 1)

Various muteins, analogs and active fragments of conantokin-G are known (collectively referred to herein as derivatives). See, e.g., Chandler et al., J. Biol. Chem., 268, pp. 17173–78 (1993); Skolnick et al., "Conantokin-G and its analogs", pp. 155–65, Direct and Allosteric Control of Glutamate Receptors, CRC Press (1994). Particularly preferred examples of these molecules are recited below:

Ala-$^7$Con-G

Ala-$^{7,10,14}$Con-G

Glu-$^{7,10,14}$Con-G

Tyr-$^7$Con-G

Ala-$^7$Tyr-$^{10}$Con-G

Tyr-$^0$Con-G

N$^\alpha$-Ac-Con-G

Glu-$^{3,4,7,10,14}$Con-G

D-Glu-$^{3,4,7,10,14}$-Arg-Con-G

Asn-$^{17}$-(OH)-Con-G

Inactive derivatives of conantokin-G are not preferred, such as those listed below.

Tyr-$^3$,Con-G (inactive)   Glu-$^4$Con-G (inactive)

The preferred con-G used in the present invention is wild type protein (and DNA encoding same), as described in SEQ. ID. NO. 1.

In another preferred embodiment, conantokin T (Con-T) is administered to produce analgesia or for neuroprotection.

Con-T Gly-Glu-Gla-Gla-Tyr-Gln-Lys-Met-Leu-Gla-Asn-Leu-Arg-Gla-Ala-Glu-Val-Lys-Lys-Asn-Ala-NH$_2$ (SEQ. ID. NO. 2)

In another preferred embodiment, conantokin (Con-R) is administered to produce analgesia or for neuroprotection.

Con-R Gly-Glu-Gla-Gla-Val-Ala-Lys-Met-Ala-Ala-Glu-Leu-Ala-Arg-Glu-Asn-Ile-Ala-Lys-Gly-Cys-Lys-Val-Asn-Cys-Tyr-Pro (SEQ. ID. NO. 3)

Derivative muteins, analogs or active fragments of the known conantokins may be synthesized according to known techniques, including conservative amino acid substitutions, such as outlined in U.S. Pat. No. 5,545,723 (see particularly col. 2, line 50—col. 3, line 8); 5,534,615 (see particularly col. 19, line 45—col. 22, line 33); and 5,364,769 (see particularly col. 4, line 55—col. 7, line 26), each herein incorporated by reference.

Additional conantokins, or their derivatives, may be conveniently assayed for activity using a [$^3$H]MK-801 binding assay. Briefly, new conantokins may be assayed for activity by their ability to attenuate the enhancement of [$^3$H]MK-801 binding to forebrain membrane preparations in the presence of an effective concentration of spermine (an NMDA polyamine site agonist having a maximal effective concentration of about 20 μM). See, e.g., Chandler et al., J. Biol. Chem., 269, pp. 17173–178 (1993), and references cited therein, herein incorporated by reference.

The conantokins useful in this invention may be isolated from natural sources and purified (see, e.g., McIntosh et al., *Arch. Biochem. Biophys.*, 218, pp.329–34 (1982). Alternatively, conantokins may produced according to any suitable method known in the art.

In a preferred embodiment, the conantokins are synthesized using FMOC chemistry. See, e.g., Rivier et al., *Biochemistry*, 26, pp. 8508–12 (1987); Chandler et al., *J. Biol. Chem.*, 269, pp. 17173–178 (1993). Briefly, N-alpha-protected amino acid hydrides are prepared in crystallized form and used for successive amino acid addition at the N-terminus. At each residue addition, the growing peptide, on a solid support, is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue addition step, the amino acid addition reaction may be repeated for a total of two or three separate addition reactions, to increase the percentage of growing peptide molecules which are reacted. Typically, 1–2 reaction cycles are used for the first twelve residue additions, and 2–3 reaction cycles for the remaining residues. See, e.g., U.S. Pat. Nos. 5,587,454 and 5,364,842, each herein incorporated by reference.

After completing the growing peptide chains, the protected peptide is treated with liquid hydrofluoric acid to deblock and release the peptides from the support. For preparing an amidated peptide, the resin support used in the synthesis can be selected to supply a C-terminal amide, after peptide cleavage from the resin.

In particular, peptides may be synthesized on a MilliGen 9050 automated peptide synthesizer using FMOC chemistry. Amino acids are coupled with a four-fold excess of pentafluorophenyl esters. FMOC-Gla(diO'-Bu)-OH was coupled with less molar excess (2 to 2.5 fold) to reduce cost. Peptides are cleaved from the solid support with trifluoroacetic acid containing 5% of thioanisole as a scavenger. The peptides are precipitated with ethyl ether and purified with reverse-phase HPLC. The integrity of the peptides is verified by amino acid analysis and fast atom bombardment mass spectroscopy. Synthesis of conantokin-G, and various derivatives thereof, is specifically described by Chandler et al., *J. Biol. Chem.*, 269, pp.17173–178 (1993).

Cell based recombinant production of conantokins is contemplated, provided that the cell line used for production is capable of carrying out the necessary gamma-carboxylations.

A gene of interest (i.e., a gene that encodes a suitable conantokin) can be inserted into a cloning site of a suitable expression vector by using standard techniques. These techniques are well known to those skilled in the art.

The expression vector containing the gene of interest may then be used to transfect the desired cell line. Standard transfection techniques such as calcium phosphate co-precipitation, DEAE-dextran transfection or electroporation may be utilized. Commercially available mammalian transfection kits may be purchased from e.g., Stratagene.

A wide variety of host/expression vector combinations may be used to express a gene encoding a conantokin of interest. See, e.g., U.S. Pat. No. 5,545,723, herein incorporated by reference, for suitable cell-based production expression vectors.

A wide variety of cells may be used, provided that the cells can carry out any necessary gamma-carboxylations. The gamma carboxylation is typically carried out by a vitamin K-dependent carboxylase activity. Useful cells include well known, publically available immortalized cell lines as well as dividing primary cell cultures. Among the useful cells are those that normally carry out such gamma-carboxylations. There are numerous kidney cells or liver cells (i.e., hepatocyte or hepatocyte-derived cells) that normally carry out vitamin K dependent gamma-carboxylation of glutamic acid residues. See, e.g., Walls et al., *Gene*, 81, pp. 139–49 (1989) (kidney cell line 293); Anson et al., *Nature*, pp. 683–85 (1985) (rat hepatoma cell line, H4-11-E-C3, clone 4A).

Alternatively, cells may be genetically engineered to carry out the necessary gamma-carboxylations. See, e.g., Berg et al., *Exp. Cell Res.*, 192, pp. 32–40 (1991) (BHK cells transformed with human adenovirus), incorporated herein by reference.

Increased expression can be achieved by increasing or amplifying the transgene copy number using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841), all herein incorporated by reference.

Administration of conantokins according to this invention may be achieved using any suitable delivery means, including:

(a) pump (see, e.g., *Annals of Pharmacotherapy*, 27:912 (1993); *Cancer*, 41:1270 (1993); *Cancer Research*, 44:1698 (1984), incorporated herein by reference), (b), microencapsulation (see, e.g., U.S. Pat. Nos. 4,352,883; 4,353,888; and 5,084,350, herein incorporated by reference), (c) continuous release polymer implants (see, e.g., Sabel, U.S. Pat. No. 4,883,666, incorporated herein by reference), (d) macroencapsulation (see, e.g., U.S. Pat. Nos. 5,284,761, 5,158,881, 4,976,859 and 4,968,733 and published PCT patent applications WO92/19195, WO 95/05452, each incorporated herein by reference);

(e) naked or unencapsulated cell grafts to the CNS (see, e.g., U.S. Pat. Nos. 5,082,670 and 5,618,531, each incorporated herein by reference); or (f) injection, either subcutaneously, intravenously, intra-arterially, intramuscularly, or to other suitable site;

(g) oral administration, in capsule, liquid, tablet, pill, or prolonged release formulation.

In one embodiment of this invention, a conantokin is delivered directly into the CNS, preferably to the brain ventricles, brain parenchyma, the intrathecal space or other suitable CNS location, most preferably intrathecally.

For the treatment of pain, if the route of administration is directly to the central nervous system, the dosage contemplated is between about 1 ng–100 mg per day, preferably between about 100 ng–10 mg per day, most preferably between 1 $\mu$g and 100 $\mu$g per day. If administered peripherally (e.g., orally, subcutaneously or intravenously, preferably intravenously), the dosage contemplated is somewhat higher, between about 100 ng–1000 mg per day, preferably between about 10 $\mu$g–100 mg per day, most preferably between 100 $\mu$g and 10 mg per day.

If the conantokin is administered by continuous infusion (i.e., by pump delivery, bioerodable polymer delivery or cell-based delivery), then a lower dosage is contemplated than for bolus delivery.

In addition to administration of conantokin for production of analgesia, this invention contemplates administration of a conantokin NMDA antagonist in combination with opioid therapy, to prevent development of tolerance resulting from continuous infusion of opioids.

For neuroprotection against excitotoxicity mediated at least in part by NMDA receptors, similar dosages as outlined above for treatment of pain are contemplated if delivered directly to the central nervous sytem. Higher dosages are contemplated for peripheral delivery, up to 10,000 mg per day. For neuroprotection applications, such as stroke or traumatic brain injury, we prefer intravenous or intra-arterial administration.

Excitotoxicity has been implicated in a variety of pathological conditions including epilepsy, stroke, ischemia, and neurodegenerative diseases such as Huntington's disease, Parkinson's disease and Alzheimer's disease. Accordingly, conantokins may provide one means of preventing the cell loss and associated behavioral abnormalities of these and possibly other human disorders. Use of conantokins according to this invention may be a safe and practical therapeutic approach for protecting patients suffering from a number of human neurodegenerative disorders characterized by neuronal cell death or damage due to excitotoxicity mediated at least in part by NMDA receptors (i.e., neuroprotection).

Huntington's disease (HD) is an autosomal dominant neurodegenerative disease characterized by a relentlessly progressive movement disorder with devastating psychiatric and cognitive deterioration. HD is associated with a consistent and severe atrophy of the neostriatum which is related to a marked loss of the GABAergic medium-sized spiny projection neurons, the major output neurons of the striatum. Intrastriatal injections of excitotoxins such as quinolinic acid (QA) mimic the pattern of selective neuronal vulnerability seen in HD. QA lesions result in motor and cognitive deficits which are among the major symptoms seen in HD. Thus, intrastriatal injections of QA have become a useful model of HD and can serve to evaluate novel therapeutic strategies aimed at preventing, attenuating, or reversing neuroanatomical and behavioral changes associated with HD.

The methods of this invention are intended for use in a mammalian host, recipient, patient, subject or individual, preferably a primate, most preferably a human.

If the conantokin is administered using encapsulated cells, we prefer macroencapsulation, as described in U.S. Pat. Nos. 5,284,761, 5,158,881, 4,976,859 and 4,968,733 and published PCT patent applications WO92/19195, WO 95/05452, each incorporated herein by reference. Cell number in the devices can be varied; preferably each device contains between $10^3$14 $10^9$ cells, most preferably $10^5$ to $10^7$ cells. A large number of macroencapsulation devices may be implanted in the patient; we prefer between one to 10 devices.

EXAMPLES

Example 1

Administration of Con-G in Rat Model

The in vivo activity of conantokins (polyamine site NMDA antagonists) was evaluated in the formalin test of acute and tonic pain. Since MK-801 (ion channel NMDA antagonist) only has a submaximal analgesic effect and ifenprodil (a polyamine site NMDA antagonist) had no effect at a high in the formalin test, it was not known whether the conantokins would have analgesic activity in the formalin test.

Animals:

All experimental procedures were approved by the Institutional Animal Care and Use Committee and conducted in compliance with the American Association for accreditation of Laboratory Animal Care. Male Sprague-Dawley rats 275–350 g from Taconic Farms (Germantown, N.Y.) were used in these studies. The animals were housed individually in a temperature and humidity-controlled colony room which was maintained on a 12 hr light/dark cycle with lights on at 0700 hrs. Food and water were available ad libitum throughout the experiment.

Intrathecal Cannula Placement:

The rats were anesthetized using Nembutal at 50 mg/kg and the back of the neck was shaved and prepped. The rat was placed in a stereotaxic apparatus with the neck flexed downward. A small cross incision was made through the skin at the back of the skull. The dura membrane is exposed using the retractors and the area was cleaned with cotton tips. A small pin incision was made through the dura membrane and the PE-10 tubing is inserted caudally 8.5 cm with the tip reaching L4,5. The catheter was secured in place to the skull with superglue at a knot that has dental acrylate. This catheter was exteriorized out the back of the neck at a location that was inaccessible to the rat. Following surgery, the skin was sutured and animals were monitored until fully awake.

Drugs for Testing:

The drugs used in this study included human β-endorphin (Sigma), MK-801 (Research Biochemicals, Nattick, Mass.), conantokin G (Peptide Institute, Osaka, Japan) and conantokin R (gift from Cognetix, Salt Lake City,Utah.).

Formalin Testing:

To perform the formalin test, we used methods substantially similar to those described in Hunter and Singh, "Role of excitatory amino acid receptors in the mediation of the nociceptive response to formalin in the rat", *Neurosci. Lett.*, 174, pp. 217–221 (1994) and Yamamoto and Yaksh, "Comparison of the antinociceptive effects of pre- and posttreatment with intrathecal morphine and MK801, an NMDA antagonist, on the formalin test in the rat", *Anesthesiol.*, 77, pp. 757–763 (1992).

Briefly, fifty µl of 5% formalin was injected subcutaneously (s.c.) into the dorsal surface of the left hindpaw with a 30 ga needle, 10 min after i.t infusion. Either 10 µl of drug or saline was administered, followed by a 10 µl saline flush. Immediately after formalin injection, the animal was placed in a cage and observed for an 88 min period. Spontaneous hindpaw flinches were recorded for 1 minute periods for the first minute and at 8 minute intervals thereafter.

Typically, the formalin response occurs in two distinct phases: phase 1 during the first minute following formalin injection, followed by a quiescent phase for approximately 15 min, and phase 2 which begins at 15–20 min, peaks around 40 min, and lasts for about 1 hour, gradually subsiding thereafter. It is thought that the early phase involves direct activation of primary afferent input to the spinal cord, similar to acute pain responses, while the latter phase represents a more prolonged, tonic pain response involving central sensitization mechanisms. Following behavioral observations, the rats were sacrificed.

Opioid Agonist Alone:

β-endorphin showed a dose-dependent decrease in flinches in both phase I and phase II. FIG. 1. There was a lower dose of β-endorphin required to inhibit phase I flinches (0.3 µg) versus phase II flinches (0.6 µg). There was no effect of β-endorphin at (0.15 µg) on phase I flinches and (0.3 µg) on phase II flinches. Maximal possible effect was observed in phase I at 1.0 µg and phase II at 3.3 µg of β-endorphin with the 3.3 µg dose leading to overt signs of sedation and motor impairment.

Figure 2:
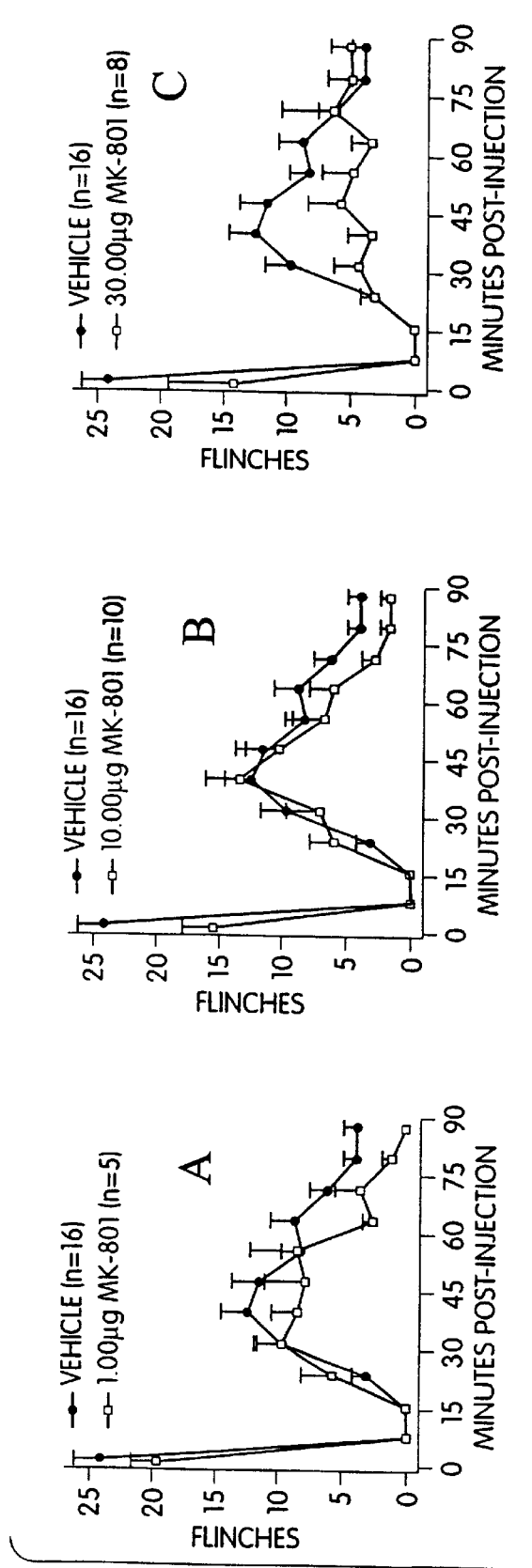
FIGS. 2A–C shows results (plotted as hindpaw flinches versus time) in the formalin test for pain comparing MK-801 and controls, for dosages of MK-801 of 1.00 μg (Panel A), 10.00 μg (Panel B), 30.00 μg (Panel C).

NMDA Antagonists:

A 30 µg dose of MK-801 was required to significantly attenuate Phase II flinches (FIG. 2)—at this dose there were side effects, including head weaving. There was clear toxicity associated with MK-801 at doses that decreased flinches.

Figure 3:
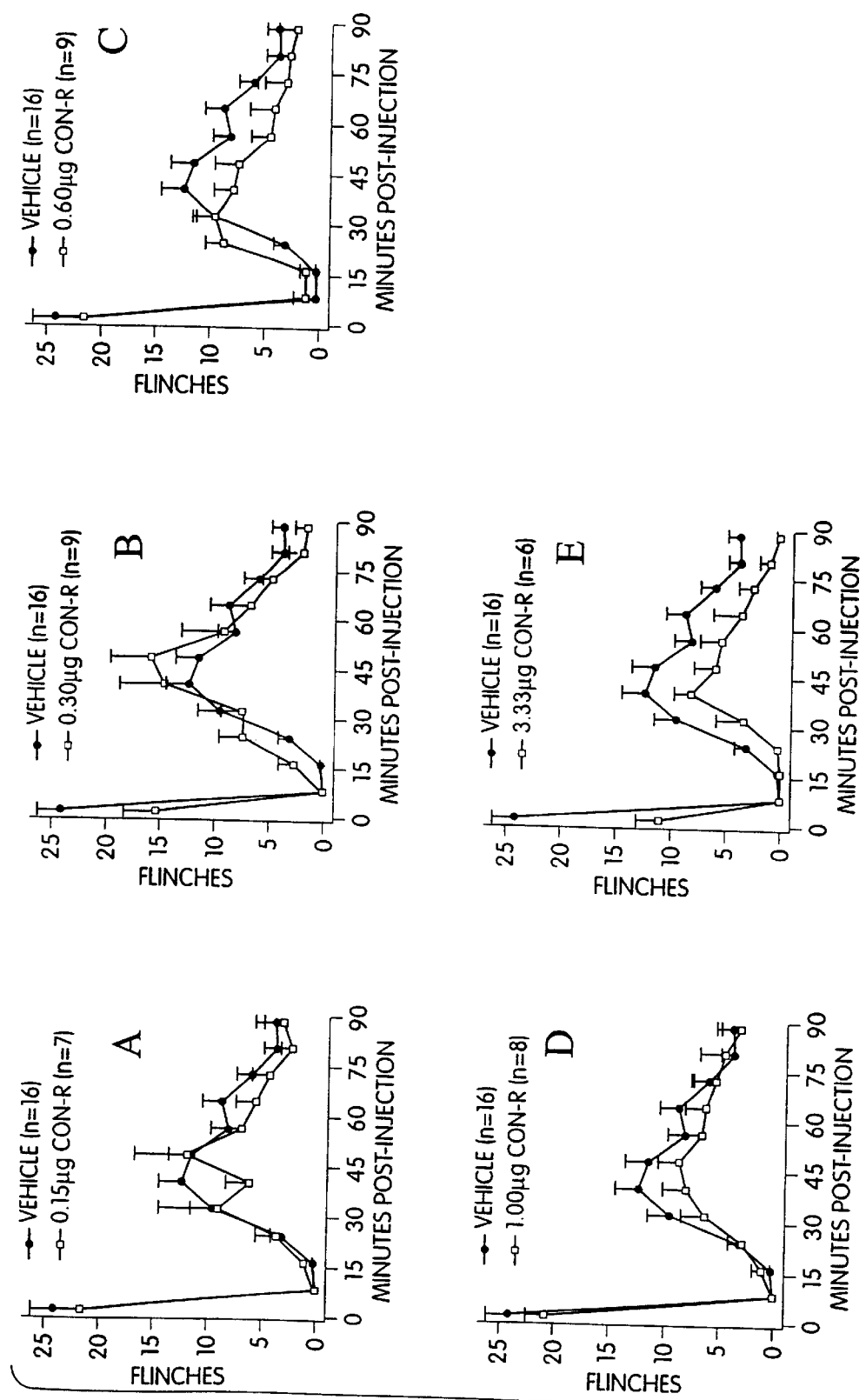
FIGS. 3A–E shows results (plotted as hindpaw flinches versus time) in the formalin test for pain comparing conantokin R and controls, for dosages of conantokin-R of 0.15 μg (Panel A), 0.30 μg (Panel B), 0.60 μg (Panel C), 1.00 μg (Panel D) and 3.33 μg (Panel E).
Figure 6:
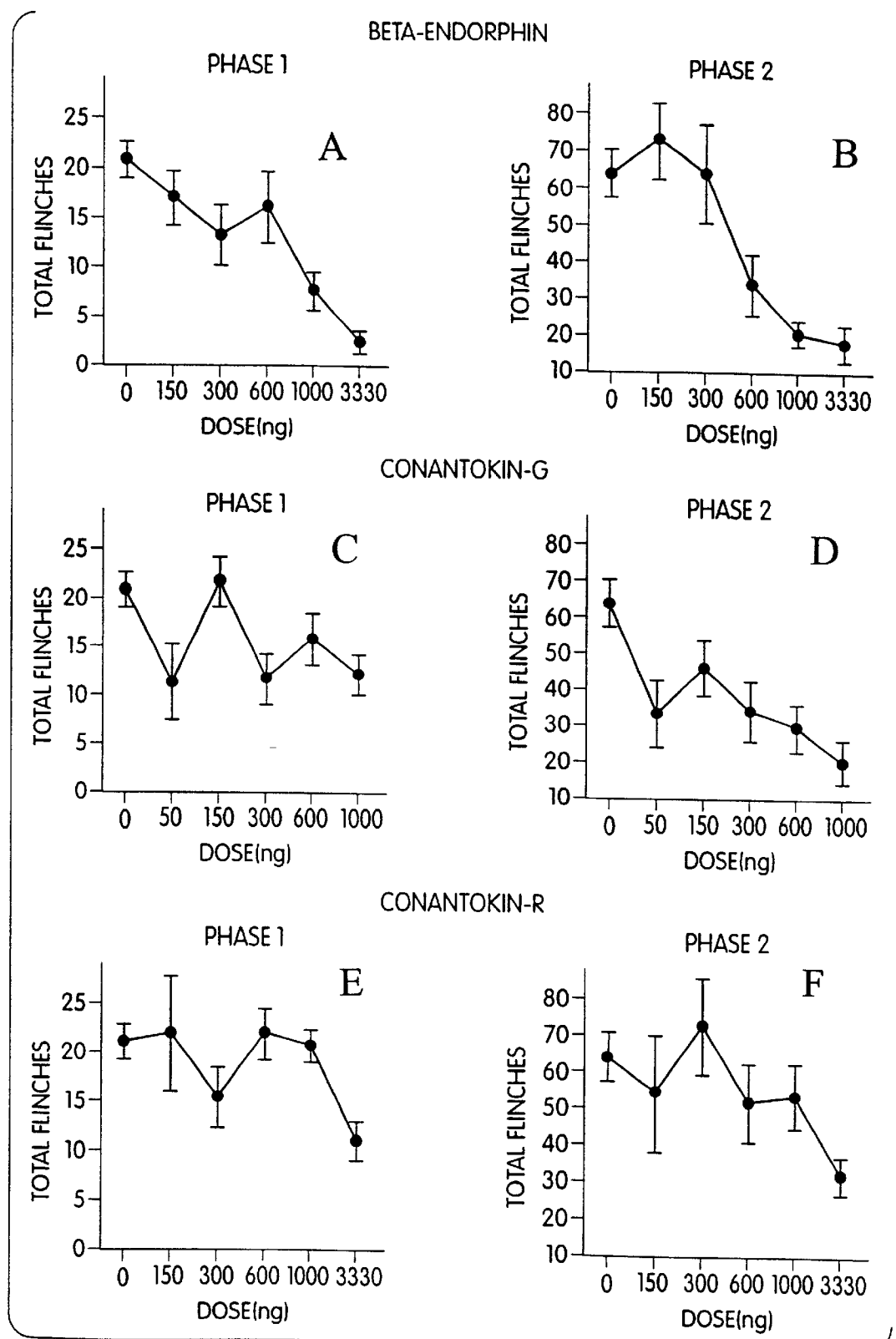
FIGS. 6A–F shows a summary of the results (plotted as hindpaw flinches versus dosage) in the formalin test for pain for each of beta-endorphin (Panels A and B), conantokin-G (Panels C and D), and conantokin-R (Panels E and F)

Conantokin R was effective in attenuating both phase I and phase II flinches at a 3.3 µg dose. FIGS. 3 and 6. Conantokin R required more than 3.3 µg i.t. to induce analgesic effects in both acute and tonic pain portions of the testing. One of six rats tested with the highest dose of conantokin R (3.3 µg) showed signs of incoordination.

Figure 5:
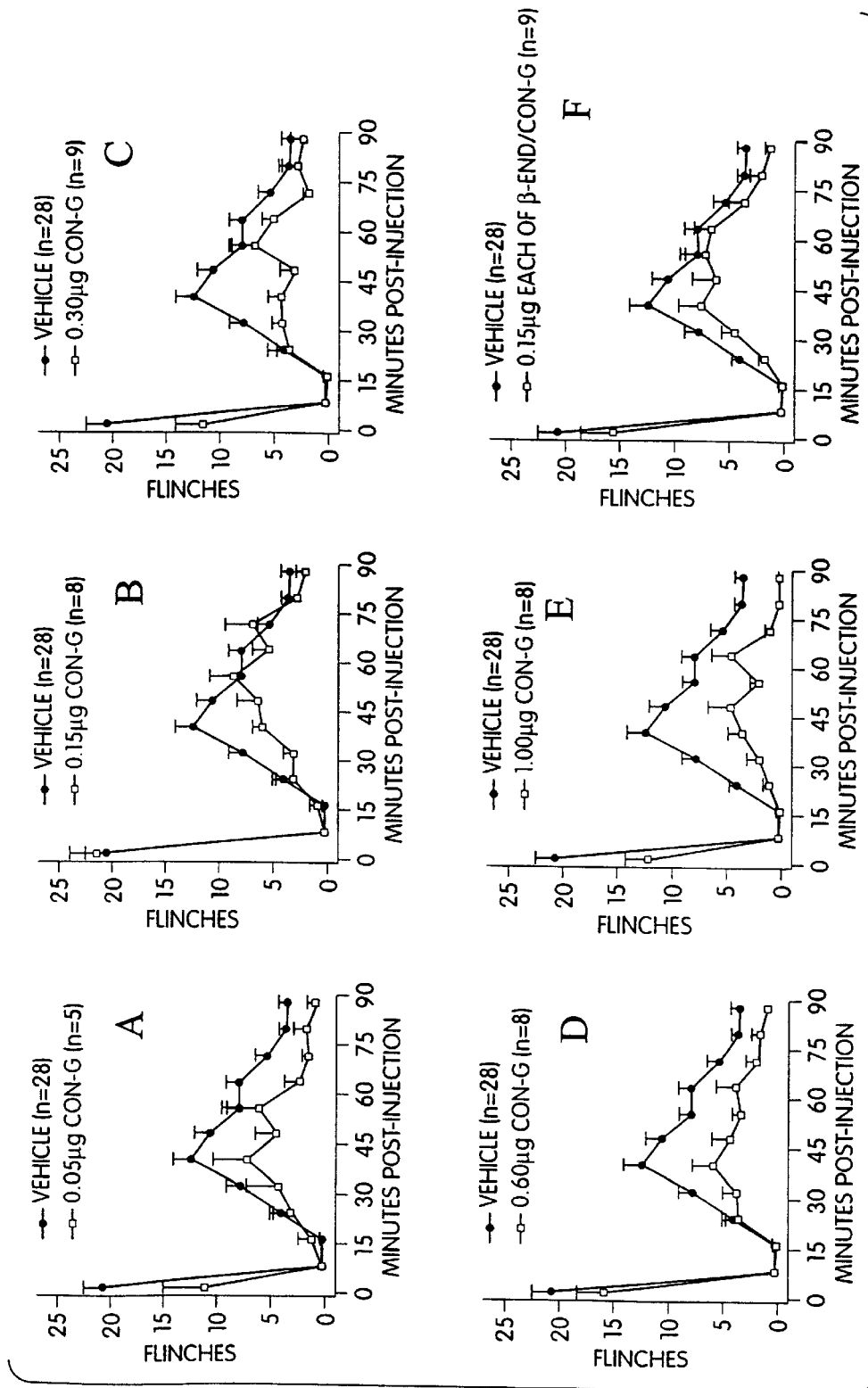
FIGS. 5A–F shows results (plotted as hindpaw flinches versus time) in the formalin test for pain comparing conantokin G and controls, for dosages of conantokin-G of 0.05 μg (Panel A), 0.15 μg (Panel B), 0.30 μg (Panel C), 0.60 μg (Panel D) and 1.00 μg (Panel E). This figure also shows the results obtained administering conantokin G and beta endorphin in combination at a dose of each of 0.15 μg panel F.

Conantokin G was found to be very potent in decreasing phase II versus phase I flinches. FIGS. 5 and 6. Only 0.05 µg of conantokin G were required to significantly attenuate phase II flinches and 0.6 µg nearly abolished phase II flinches without significantly decreasing phase I flinches. A 1.0 µg dose of conantokin G did significantly attenuate phase I flinches. Conantokin G was analgesic in both phase I (acute pain) and phase I (tonic pain) of the formalin test in rats when given intrathecally (i.t.) at doses of 0.05–1 µg with an ED50 of 0.15 µg in phase II. There were no overt signs of toxicity at any dose of conantokin G.

Figure 4:
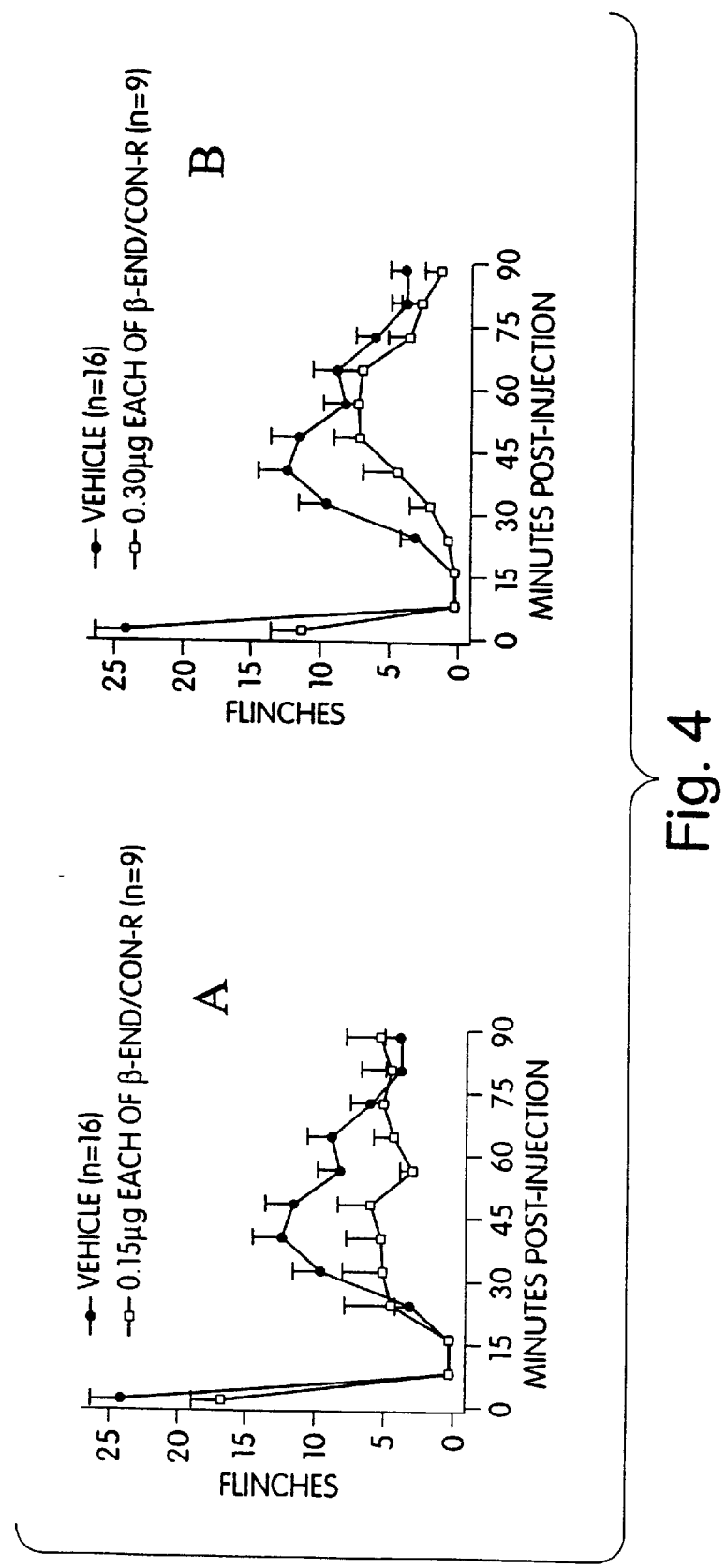
FIGS. 4A–B shows results (plotted as hindpaw flinches versus time) in the formalin test for pain comparing conantokin R combined with beta-endorphin and controls, for dosages of each of conantokin-R and beta-endorphin of 0.15 μg (Panel A) and 0.30 μg (Panel B).

Combining NMDA Antagonist with β-Endorphin:

Conantokin R and β-endorphin were combined at 0.15 µg or 0.3 µg each which resulted in an at least an additive analgesic effect in phase I phase II. FIG. 4. There was no effect of conantokin R or β-endorphin at 0.15 or 0.3 µg alone, yet there was a significant decrease in phase II flinches when 0.15 µg of each were combined.

The combination of conantokin G with β-endorphin resulted in reduced flinches that was no different from conantokin G alone. FIG. 5.

The analgesic effects of these conantokin polyamine site NMDA receptor antagonists were more potent in tonic versus acute pain.

Based on the present study, we conclude that that the conantokin family of NMDA polyamine site antagonists may be useful analgesic substances that appear to have little toxicity at analgesic doses. Further, these data suggest that conantokins may be relatively safe and effective agents in the treatment of persistent pain due to tissue or nerve injury. In addition, the antinociceptive effect of the conantokins in phase I suggests that they may be effective analgesics for acute pain.

Example 2

Construction of a Conantokin-G Cell Line

A cell line secreting con-G is constructed as follows. Plasmid pPI-DN uses the phosphoglycerate kinase promoter driving the gene of interest (i.e. a cDNA encoding conantokin-G). Other genes present on this plasmid include the ampicillin resistance gene (for selection in E. coli), the neomycin resistance gene(for selection in mammalian cells), and the mutant dihydrofolate reductase gene (for amplification in methotrexate, MTX).

A BHK cell line is transformed with human adenovirus and a plasmid containing a cDNA encoding conantokin-G, substantially as described in Berg et al. *Exp. Cell Res.*, 192, pp. (1991) to produce a cell line that produces correctly gamma-carboxylated conantokin-G.

Approximately 100,000 stock BHK cells are plated into a 10 $cm^2$ dish. The pPI-DN vector carrying the con-G cDNA is transfected using a standard protocol for CaPO4 transfection with a Stratagene Mammalian Transfection kit. Cells were placed in selective medium three days later, consisting of DMEM (Gibco) supplemented with 10% FBS (Gibco, lot #42K2445), 2mM glutamate and 1 mg/ml G418. After two weeks in this selective medium, the cells are amplified via sequential exposure to increasing levels of methotrexate (MTX) in the series 1, 5, 10, 20, 50, 100, and 200 μM. After two weeks in 200 μM MTX, cells are maintained in DMEM supplemented with 10% FBS and 50 mM MTX. After the initial G418 selection, this cell line is not grown in the presence of antibiotics.

Example 3

Encapsulation

If encapsulated cells are used to deliver the conantokin, conantokin-secreting cells may be encapsulated according to the following procedure:

The hollow fibers are fabricated from a polyether sulfone (PES) with an outside diameter of 720 μm and a wall thickness of a 100 μm (AKZO-Nobel Wüppertal, Germany). These fibers are described in U.S. Pat. Nos. 4,976,859 and 4,968,733, herein incorporated by reference. In some studies we use a PES#5 membrane which has a MWCO of about 280 kd. In other studies we use a PES#8 membrane which has a MWCO of about 90 kd.

The devices typically comprise:

1) a semipermeable poly (ether sulfone) hollow fiber membrane fabricated by AKZO Nobel Faser AG;
2) a hub membrane segment;
3) a light cured methacrylate (LCM) resin leading end; and
4) a silicone tether.

The semipermeable PES membrane used typically has the following characteristics:

| | |
|---|---|
| Internal Diameter | 500 ± 30 μm |
| Wall Thickness | 100 ± 15 μm |
| Force at Break | 100 ± 15 cN |
| Elongation at Break | 44 ± 10% |
| Hydraulic Permeability | 63 ± 8 (ml/min $m^2$ mmHg) |
| nMWCO (dextrans) | 280 ± 20 kd |

The components of the device are commercially available. The LCM glue is available from Ablestik Laboratories (Newark, DE); Luxtrak Adhesives LCM23 and LCM24). The tether material is available from Specialty Silicone Fabricators (Robles, Calif.). The tether dimensions are 0.79 mm OD×0.43 mm ID×length 202 mm. The morphology of the device is as follows: The inner surface has a permselective skin. The wall has an open cell foam structure. The outer surface has an open structure, with pores up to 1.5 μm occupying 30±5% of the outer surface.

Fiber material is first cut into 5 cm long segments and the distal extremity of each segment sealed with a photopolymerized acrylic glue (LCM-25, ICI). Following sterilization with ethylene oxide and outgassing, the fiber segments are loaded with a suspension of about $2\times10^5$ transfected cells in a collagen solution (Zyderm® soluble bovine collagen) via a Hamilton syringe and a 25 gauge needle through an attached injection port. The proximal end of the capsule is sealed with the same acrylic glue. In some studies we use a collagen matrix (e.g., Zyplast™); in other studies we use agarose or chitosan. The volume of the device contemplated in the human studies is approximately 15–18 μl.

A silicone tether (Specialty Silicone Fabrication, Taunton, Me.) (ID: 690 μm; OD: 1.25 mm) is placed over the proximal end of the fiber allowing easy manipulation and retrieval of the device.

Example 4

Neuroprotective Effects of Conantokin-G

This study quantified the extent of neuroprotection provided by conantokin G (Con-G) as a result of quinolinic acid (QA). Rats were pretreted with either Con-G (10 µg) or vehicle in the right striatum followed 10 min. later by QA (200 nmoles) into the ipsilateral striatum. Two weeks later, the rats had their striata removed. Choline acetyltransferase (ChAT) and gamma amino decarboxylase (GAD) enzyme activity were measured to quantify damage and neuronal cell loss of cholinergic and GABAergic neurons, respectively.

There was a significant loss of ChAT (32%) and GAD (40%) activity in the ipsilateral striatum of control rats. This neuronal loss was completely blocked by Con-G pretreatment. This data suggets that Con-G has a neuroprotective effect against excitotoxic neuronal cell damage and cell death.

The role of excitotoxic damage in the etiology of neurodegenerative disease is well established. This data suggests that conantokin-G would be useful for the treatment of neurodegenerative diseases characterized by excitotoxicity mediated at least in part by NMDA receptors.

Animal Subjects:

Adult male Sprague-Dawley rats (Taconic Breeders, Germantown, N.Y.) approximately 6 months old and weighing 350–450 grams were used in these studies. The animals were housed in groups of 3–4 in a temperature and humidity-controlled colony room which was maintained on a 12 hr light/dark cycle with lights on at 0700 hrs. Food and water were available ad libitum throughout the experiment. All experimentation was conducted in accord with NIH guidelines.

Surgery:

Immediately prior to surgery, rats were anesthetized with sodium pentobarbital (45 mg/kg, i.p.), and positioned in a Kopf stereotaxic instrument at the coordinates for the striatum: 1.2 mm anterior to Bregma, 2.6 mm lateral to the sagittal suture, and 3.5 mm ventral to the surface of the brain (Paxinos and Watson, 1980). A midline incision was made in the scalp and a hole drilled for the injection of vehicle or 10 µg Con-G in 10 µl. The solution was infused into the striatum using a 28-gauge Hamilton syringe over a 2 minute period. 5 minutes later, all animals are injected with 200 nmoles of QA (Sigma Chemical Co.) into the same ipsilateral striatum at the same identical coordinates. Injections of QA were made in a 1 µl volume over five minutes. The injection cannula was left in place for an additional two minutes to allow the QA to diffuse from the needle tip. The skin was then re-sutured.

Neurochemistry:

Immediately following capsule retrieval the striata were rapidly dissected on ice and stored at −80C. prior to processing for GAD and ChAT activity. For the determination of GAD activity, frozen tissue sections were homogenized in 20 volumes (v/w) of 2 mM-Tris-maleate buffer (pH 7.4) to 2 mM EGTA. The activity was determined by a microassay based on the amount of $^{14}Co2$ released from the substrate [$^{14}C$] glutamic acid. See Legay et al., *J. Neurochem.*, 46, pp. 1478–86 (1986).

$^{14}CO2$ was trapped on a filter disc and counted by liquid scintillation spectrometry (Ecoscint O, National Diagnostics, Atlanta, GA). The incubation was performed in Falcon 12×75 mm polystyrene tube. A piece of ¼" Whatman filter disc was put on the cap. 25 µl of TS-2 (Research Products International, Mount Prospect, Ill.) was applied on it and air dried for 30 min.

The final 120 µl volume for incubation consisted of 60 µl of incubation mixture, 20 µl of DL [1-$^{14}C$] glutamic acid (New England Nuclear, Boston, Mass.) and 40 µl of brain homogenate. The incubation mixture contained in mmol/l: potassium phosphate (pH 7.4), 30; EDTA, 0.1; pyridoxal phosphate, 0.05; dithiothreitol, 0.1; L-glutamic acid, 9; with 0.5% (w/v) triton X-100.

Incubations were for 1 hr at 37° C. and were terminated by the injection of 0.1 ml of 10% (w/v) trichloroacetic acid (TCA). An additional hour at 37° C. was allowed to ensure complete release of $^{14}CO2$. Nonspecific activity was determined by stopping the reaction at time 0. Production of $^{14}CO2$ was linear with protein. GAD activity was stable for homogenates stored at −80° C. for 1 month. Specific GAD activity was calculated by subtracting the nonspecific activity from the total activity and dividing by the protein concentration.

The ChAT assay was based on the radioenzymatic method of Fonnum, *Biochem J.*, 115, pp. 465–72 (1969). A 400 µl amount of fresh homogenate from above had 50 µl of 2 mM eserine +50 µl of 5% triton X-100 added. This was vortexed and 50 µl was aliquoted for a protein assay and 50 µl was aliquoted into 5 tubes for ChAT activity with three tubes containing choline substrate and two tubes without choline substrate. The assay solution for the ChAT assay contained the following in mM: NaCl 300, eserine sulfate 0.1, cystein 3.4, disodium EGTA 0.5, sodium phosphate buffer (pH 7.4) 25, choline chloride 10 (only in 3 tubes), and [$^{14}C$]acetyl-CoA 0.3 (0.3 mCi/mMol, New England Nuclear, Boston, Mass.) in a final volume of 200 µl containing 50 µl of homogenate. A 150 µl aliquot of ice cold assay solution was added to 50 µl of the tissue homogenate and this was transferred to a 37° C. water bath for 30 min. The incubation was stopped by 500 µl of ice cold 3-heptanone +20 mg/ml tetraphenylboron solution. The tubes were vortexed and placed back on ice. 300 µl of the organic phase was sampled for quantification of carbon-14 incorporated into ACh. ChAT activity was determined as the net synthesis of [$^{14}C$] ACh occurring in the presence minus the absence of choline and normalized by mg protein. The final values were represented as nmoles ACh/mg protein×hr.

Neurochemistry

Figure 7:
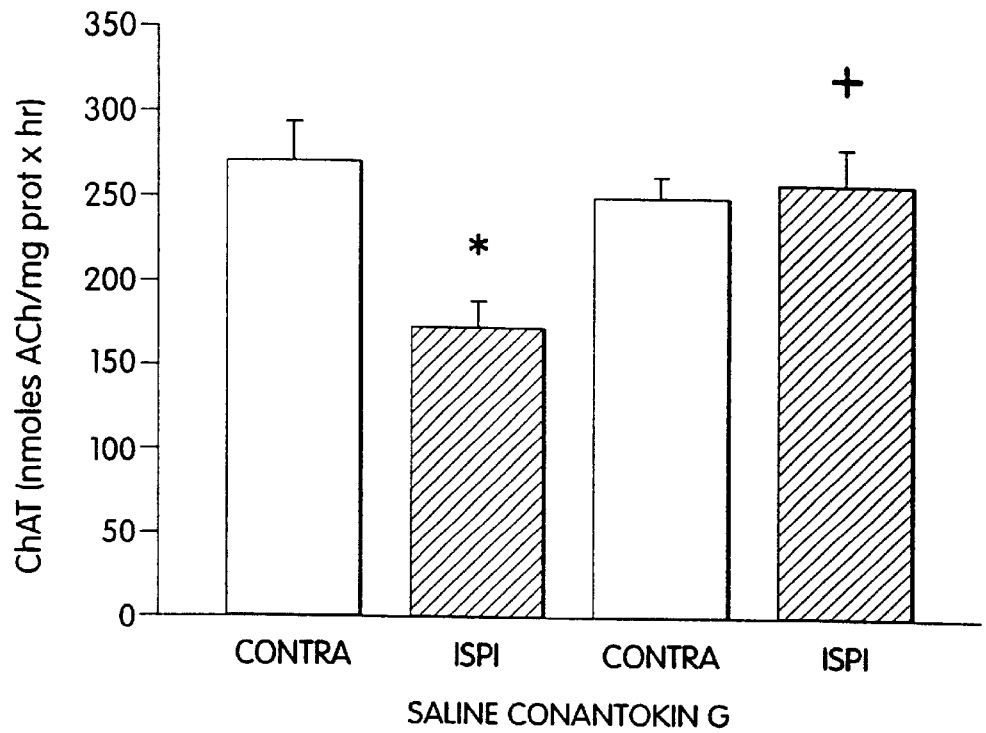
FIG. 7 shows striatal ChAT enzyme activity levels for the QA lesioned ipsilateral striatum compared to the unlesioned contralateral striatum, when pre-treated with either saline (control) or conantokin-G.
Figure 8:
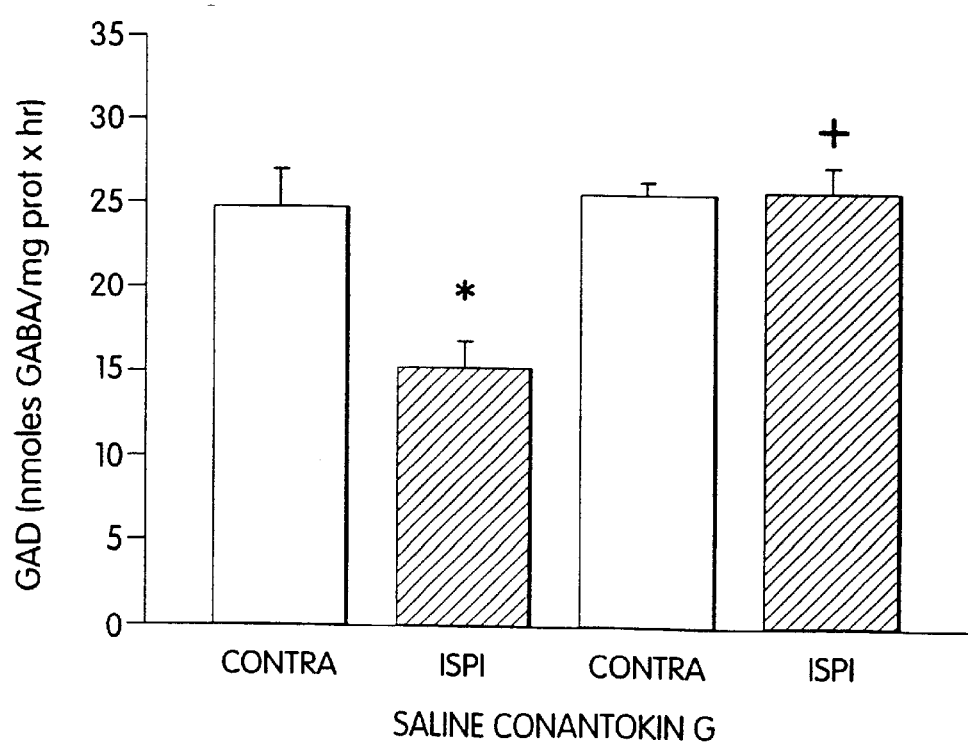
FIG. 8 shows striatal GAD enzyme activity levels for the QA lesioned ipsilateral striatum compared to the unlesioned contralateral striatum, when pre-treated with either saline (control) or conantokin-G.

The QA lesioned striatal ChAT and GAD enzyme activity levels were reduced by 33±8% and 40±7%, respectively, compared to the unlesioned contralateral striatum (FIGS. 7 and 8).

The ChAT activity was similar in both groups: unlesioned striatum with Saline group=270±22 nmoles ACh/mg prot×hr and Con-G=249±42 nmoles ACh/mg prot×hr ($F(1,15)$; Scheffe F=.316, p>.05).

The GAD activity was also similar in both groups: unlesioned striatum with Saline group=25±2 nmoles GABA/mg prot×hr and Con-G=25±1 nmoles GABA/mg prot×hr ($F(1,15)$; Scheffe F=.043, p>.05).

Con-G pretreatment completely blocked the QA lesion-induced loss of ChAT activity compared to controls ($F(3, 31)=20.29$, Scheffe p<.01). FIG. 7. Similarly, there was also a complete prevention of the loss of GAD activity ($F(3,31)= 7.85$, Scheffe p<.01). FIG. 8.

The results of this study demonstrate that Con-G can prevent, in part, the neuroanatomical and neurochemical sequelae seen in an animal model of HD. In rats implanted with BHK-control cells, QA injections produced a marked striatal atrophy together with a loss of cholinergic and GABAergic neurons as indicated by a loss of ChAT and GAD enzyme activity. In summary, the present results indicate that Con-G prevents striatal loss of GABAergic and cholinergic neurons as a consequence of QA administration.

What is claimed is:

1. A system for producing analgesia in a mammal suffering from pain, the system comprising at least one biocompatible device, each device comprising:
   a core of living cells secreting a conantokin;
   a jacket surrounding the core, the jacket comprising a biocompatible material; the system producing a therapeutically effective amount of the conantokin when said system is implanted into the mammal.

2. The system of claim 1 wherein the system comprises between one and ten devices.

3. The system of claim 1 wherein the conantokin is selected from the group consisting of conantokin-G, conantokin-T, conantokin-R, conantokin-Si, and conantokin-Oc, and derivatives of the foregoing conantokins.

4. The system of claim 1 wherein said mammal is a human.

5. A system for protecting a mammal from neuronal damage due to excitotoxicity mediated at least in part by NMDA receptors, the system comprising at least one biocompatible device, each device comprising:
   a core of living cells secreting a conantokin;
   a jacket surrounding the core, the jacket comprising a biocompatible material; the system producing a therapeutically effective amount of the conantokin when said system is implanted into the mammal.

6. The system of claim 5 wherein the system comprises between one and ten devices.

7. The system of claim 5 wherein the conantokin is selected from the group consisting of conantokin-G, conantokin-T, conantokin-R, conantokin-Si, and conantokin-Oc, and derivatives of the foregoing conantokins.

8. The system of claim 5 wherein said mammal is a human.

* * * * *

```
                              SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 17 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (vi) ORIGINAL SOURCE:
          (A) ORGANISM: conantokin-G (xi) SEQUENCE DESCRIPTION: SEQ ID NO:1:

Gly Glu Xaa Xaa Leu Gln Xaa Asn Gln Xaa Leu Ile Arg Xaa Lys Ser
1               5                   10                  15

Asn (2) INFORMATION FOR SEQ ID NO:2:

(i) SEQUENCE CHARACTERISTICS:
          (A) LENGTH: 21 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (vi) ORIGINAL SOURCE:
          (A) ORGANISM: conantokin-T (xi) SEQUENCE DESCRIPTION: SEQ ID NO:2:

Gly Glu Xaa Xaa Tyr Gln Lys Met Leu Xaa Asn Leu Arg Xaa Ala Glu
1               5                   10                  15

Val Lys Lys Asn Ala
            20

(2) INFORMATION FOR SEQ ID NO:3:

(i) SEQUENCE CHARACTERISTICS:
          (A) LENGTH: 27 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (vi) ORIGINAL SOURCE:
          (A) ORGANISM: conantokin-R
```

-continued (xi) SEQUENCE DESCRIPTION: SEQ ID NO:3:

```
Gly Glu Xaa Xaa Val Ala Lys Met Ala Ala Glu Leu Ala Arg Glu Asn
1               5                   10                  15
Ile Ala Lys Gly Cys Lys Val Asn Cys Tyr Pro
            20                  25
```